(12) United States Patent
Russell et al.

(10) Patent No.: US 6,632,800 B1
(45) Date of Patent: Oct. 14, 2003

(54) SYSTEM FOR MONITORING THE EXPRESSION OF TRANSGENES

(75) Inventors: Stephen James Russell, Rochester, MN (US); Kah Whye Peng, Singapore (SG)

(73) Assignee: Mayo Foundation for Medical Education and Research, Rochester, MN (US)

(*) Notice: Subject to any disclaimer, the term of this patent is extended or adjusted under 35 U.S.C. 154(b) by 34 days.

(21) Appl. No.: 09/639,667

(22) Filed: Aug. 16, 2000

Related U.S. Application Data
(60) Provisional application No. 60/149,168, filed on Aug. 17, 1999.

(51) Int. Cl.[7] .............................................. A61K 31/70
(52) U.S. Cl. ...................................................... 514/44
(58) Field of Search .............................. 514/44; 435/6, 435/320.1, 172.3, 69.7, 69.8

(56) References Cited

U.S. PATENT DOCUMENTS

| | | | |
|---|---|---|---|
| 5,631,237 A | 5/1997 | Dzau et al. | |
| 5,661,032 A | 8/1997 | Miller et al. | |
| 5,703,056 A | * 12/1997 | Blasberg et al. | ............... 514/44 |
| 5,738,985 A | 4/1998 | Miles et al. | |

OTHER PUBLICATIONS

Abai et al., "Insulin Delivery with Plasmid DNA," *Human Gene Ther.*, 1999, 10:2637–2649.
Appelros et al., "Activation peptide of carboxypeptidase B in serum and urine in acute pancreatitis," *Gut*, 1998, 42:97–102.
Bae et al., "Genomic Differences between the Diabetogenic and Nondiabetogenic Vairants of Encephalomyocarditis Virus," *Virology*, 1989, 170:282–287.
Berg et al., "Physiological functions of endosomal proteolysis," *Biochem. J.*, 1995, 307:313–326.
Cohen et al., "Complete nucleotide sequence of an attenuated hepatitis A virus: Comparison with wild–type virus," *Proc. Natl. Acad. Sci. USA*, 1987, 84:2497–2501.
de Felipe et al., "Use of the 2A sequence from foot–and–mouth disease virus in the generation of retroviral vectors for gene therapy," *Gene Therapy*, 1999, 6:198–208.
Duechler et al., "Evolutionary relationships within the human rhinovirus genus: Comparison of serotypes 89, 2, and 14," *Proc. Natl. Acad. Sci. USA*, 1987, 84:2605–2609.
Douglass et al., "Polyprotein Gene Expression: Generation of Diversity of Neuroendocrine Peptides," *Ann. Rev. Biochem.*, 1984, 53:665–715.
Earle et al., "The Complete Nucleotide Sequence of a Bovine Enterovirus," *J. Gen. Virol.*, 1988, 69:253–263.
Hooper et al., "Membrane protein secretases," *Biochem. J.*, 1997, 321:265–279.
Hughes et al., "The Complete Nucleotide Sequence of Coxsackievirus A21," *J. Gen Virol.*, 1989, 70:2943–2952.

Hutton, "Insulin secretory granule biogenesis and the pro-insulin–processing endopeptidases," *Diabetologia*, 1994, 37(Suppl. 2):S48–S56.
Iizuka et al., "Complete Nucleotide Sequence of the Genome of Coxsackievirus B1," *Virology*, 1987, 156:64–73.
Inchauspe et al., "Genomic structure of the human prototype strain H of hepatitis C virus: Comparison with American and Japanese isolates," *Proc. Natl. Acad. Sci. USA*, 1991, 88:10292–10296.
Jackson, "Initiation without an end," *Nature*, 1991, 252(6339):14–15.
Jenkins et al., "The Complete Nucleotide Sequence of Coxsackievirus B4 and Its Comparison to Other Members of the Picornaviridae," *J. Gen. Virol.*, 1987, 68:1835–1848.
Kao et al., "C–Peptide Immunochemiluminometric Assay Developed From Two Seemingly Identical Polyclonal Antisera," *Ann. Clin. Lab. Science*, 1992, 22(5):307–316.
Kato et al.,"Molecular cloning of the human hepatitis C virus genome from Japanese patients with non–A, non–B hepatitis," *Proc. Natl. Acad. Sci. USA*, 1990, 87:9524–9528.
Lynch and Snyder, "Neuropeptides: Multiple Molecular Forms, Metabolic Pathways, and Receptors," *Ann. Rev. Biochem.*, 1986, 55:773–799.
Macejak and Sarnow, "Internal initiation of translation mediated by the 5' leader of a cellular mRNA," *Nature*, 1991, 353:90–94.
McMartin, "Molecular sieving, receptor processing and peptidolysis as major determinants of peptide pharmacokinetics in vivo," *Biochem. Society Transactions*, 1989, 17(5):931–934.
Mithöfer et al., "Quantitative Assay of Trypsinogen by Measurement of Cleaved Activation Peptide after Activation with Enterokinase," *Analytical Biochem.*, 1995, 230:348–350.
Murakami and Etlinger, "Degradation of Proteins with Blocked Amino Groups by Cytoplasmic Proteases," *Biochem. Biophys. Res. Comm.*, 1987, 146(3):1249–1255.

(List continued on next page.)

*Primary Examiner*—Deborah Crouch
*Assistant Examiner*—Joseph Woitach
(74) *Attorney, Agent, or Firm*—Fish & Richardson P.C., P.A.

(57) ABSTRACT

A novel strategy for monitoring the expression of a transgene in a patient is disclosed. A marker peptide is genetically fused to either the N-terminus or C-terminus of the product of a transgene through a linker peptide which bears the recognition sequence of a host cell protease. Expression of the transgene results in release of the marker peptide into extracellular body fluid of the patient in proportion to the amount of transgene product. The level of the released marker peptide serves as an indicator of the level of transgene expression. The system is particularly useful for monitoring the expression of therapeutic transgenes and production of the therapeutic gene product.

39 Claims, 6 Drawing Sheets

OTHER PUBLICATIONS

Nagasawa et al., "Changes of Plasma Levels of Human Growth Hormone with Age in Relation to Mammary Tumour Appearance in Whey Acidic Protein/Human Growth Hormone (mWAP/hGH) Transgenic Female and Male Mice," *in vivo,* 1996, 10:503–506.

Ohara et al., "Molecular Cloning and Sequence Determination of DA strain of Theiler's Murin Encephalomyelitis Viruses," *Virology,* 1988, 164:245–255.

Okamoto et al., "Full–Length Sequence of a Hepatitis C Virus Genome Having Poor Homology to Reported Isolates; Comparative Study of Four Distinct Genotypes," *Virology,* 1992, 188:331–341.

Palmenberg et al., "The nucleotide and deducted amino acid sequences of the encephalomyocarditis viral polyprotein coding region," *Nucl. Acids Res.,* 1984, 12(6):2969–2985.

Paul et al., "The entire nucleotide sequence of the genome of human hepatitis A virus (isolate MBB)," *Virus Res.,* 1987, 8:153–171.

Pevear et al., "Analysis of the Complete Nucleotide Sequence of the Picornavirus Theiler's Murine Encephalomyelitis Virus Indicates That It Is Closely Related to Cardioviruses," *J. Virol.,* 1987, 61(5):1507–1516.

Philippou et al., "An ELISA for factor X activation peptide: application to the investigation of thrombogenesis in cardiopulmonary bypass," *Br. J. Haematol.,* 1995, 90:432–437.

Polonsky et al., "Use of Biosynthetic Human C–peptide in the Measurement of Insulin Secretion Rates in Normal Volunteers and Type I Diabetic Patients," *J. Clin. Invest.,* 1986, 77:98–105.

Racaniello and Baltimore, "Molecular cloning of poliovirus cDNA and determination of the complete nucleotide sequence of the viral genome," *Proc. Natl. Acad. Sci. USA,* 1981, 78(8):4887–4891.

Radecke et al., "Resuce of measles viruses from cloned DNA," *EMBO J.,* 1995, 14(23):5773–5784.

Rosenthal et al., "Paracrine Stimulation of Keratinocytes in Vivo and Continuous Delivery of Epidermal Growth Factor to Wounds in Vivo by Genetically Modified Fibroblasts transfected with a Novel Chimeric Construct," *in vivo,* 1997, 11:201–208.

Ryan et al., "The complete nucleotide sequence of enterovirus type 70: relationships with other members of the Picornaviridae," *J. Gen. Virol.,* 1990, 71:2291–2299.

Skern et al., "Human rhinovirus 2: complete nucleotide sequence and proteolytic processing signals in the capsid protein region," *Nucl. Acids Res.,* 1985, 13(6):2111–2126.

Smyth and Trapani, "Granzymes: exogenous proteinases that induce target cell apoptosis," *Immunol. Today,* 199516:202–206.

Sonenberg and Meerovitch, "Translation of poliovirus mRNA," *Enzyme,* 1990, 44:278–291.

Stanway et al., "Comparison of the complete nucleotide sequences of the genomes of the neurovirulent poliovirus P3/Leon/37 and its attenuated Sabin vaccine derivative P3/Leon/12a$_1$b," *Proc. Natl. Acad. Sci. USA,* 1984, 81:1539–1543.

Talanian et al., "Substrate Specificities of Caspase Family Proteases," *J. Biol. Chem.,* 1997, 272(15):9677–9682.

Thornberry et al., "A Combinationl Approach Defines Specificities of Members of the Caspase Family and Granzyme B," *J. Biol. Chem.,* 1997, 272(29):17907–17911.

Werb, "ECM and Cell Surface Proteolysis: Regulating Cellular Ecology," *Cell,* 1997, 91:439–442.

Wolfsberg et al., "Adam, a Novel Family of Membrane Proteins Containing a Disintegrin And Metalloprotease Domain: Multipotential Functions in Cell–Cell and Cell–Matrix Interactions," *J. Cell. Biol.,* 1995, 131(2):275–278.

Yamamoto et al., "Isolation of a cDNA Encoding a Human Serum Marker for Acute Pancreatitis," *J. Biol. Chem.,* 1992, 267(4):2575–2581.

\* cited by examiner

C-peptide Sequence: EAEDLQVGQVELGGGPGAGSLQPLALEGSLQKR (SEQ ID NO:24)

Fig. 6

SYSTEM FOR MONITORING THE EXPRESSION OF TRANSGENES

This application claims priority from U.S. Ser. No. 60/149,168 filed on Aug. 17, 1999.

TECHNICAL FIELD OF THE INVENTION

The invention is related to the area of gene therapy. In particular it is related to the field of expression monitoring.

BACKGROUND OF THE INVENTION

In the context of gene therapy, it is important to monitor the expression of the therapeutic transgene. The effectiveness of any genetically based therapy will be critically dependent on the kinetics of gene expression, i.e., the time of onset of gene expression and its rate of increase; the maximum level of expression and its persistence and decay; and residual long-term expression. Where the gene produces a soluble protein such as a cytokine or growth factor, gene expression often can be monitored by measuring the levels of the secreted gene product in peripheral blood. However, many therapeutic transgenes code for cell-associated proteins whose expression cannot be conveniently monitored in this way. Current approaches to monitoring the expression of cell-associated transgenes are unsatisfactory and rely on the direct sampling and immunohistochemical analysis of genetically modified tissues at various time-points following the therapeutic procedure. There is a need in the art for methods and materials that enable the monitoring of transgene expression without the requirement to sample and directly test genetically modified cells or tissues.

SUMMARY OF THE INVENTION

The invention contemplates a method of monitoring the production of a therapeutic polypeptide in a patient, comprising the steps of (a) administering to a patient in need of a therapeutic polypeptide a nucleic acid construct encoding a therapeutic polypeptide and a marker polypeptide; and (b) detecting the marker polypeptide which has been released into extracellular body fluid of the patient as an indication of the amount of therapeutic polypeptide produced from the nucleic acid construct. In some embodiments, the step of detecting is used as a qualitative or semi-quantitative test merely to determine the presence or absence of the marker peptide. The presence of the marker peptide is an indication that the transgene has been successfully delivered to the target cell, tissue, or organ of the patient. In some embodiments, the nucleic acid construct also encodes a protease-cleavable linker that is situated between the therapeutic polypeptide and the marker peptide.

The invention also provides a method for monitoring the expression of a transgene. The method comprises the steps of (a) transfecting a cell using a nucleic acid construct, (b) obtaining a biological fluid sample from a patient containing the transfected cell, and (c) quantifying a marker peptide in the sample. The nucleic acid construct comprises a transgene and a sequence encoding a marker peptide that is non-immunogenic and non-functional. The marker peptide is released from the transfected cell into extracellular body fluid of the patient. In some embodiments, the nucleic acid construct also comprises a sequence encoding a protease-cleavable linker which is positioned between the transgene and the sequence encoding a marker peptide. The level of expression of the transgene is monitored by quantifying the marker peptide in the biological fluid sample.

The invention also provides a method of monitoring the expression of a transgene in a patient, comprising the steps of: (a) transfecting a host cell ex vivo with a nucleic acid construct comprising a transgene and a sequence encoding a marker polypeptide; (b) introducing the transfected host cell into a patient; and (c) quantifying the amount of marker polypeptide which has been released into extracellular body fluid of the patient, whereby the amount of the marker polypeptide is used to monitor the level of expression of said transgene. In some embodiments, the nucleic acid construct also encodes a protease-cleavable linker which is positioned between the transgene and the coding sequence for the marker polypeptide.

The invention also provides a nucleic acid construct. The nucleic acid construct comprises a transgene and a sequence encoding a marker polypeptide that is released from the cell where it is produced into extracellular fluid. The marker polypeptide is non-immunogenic and non-functional. In some embodiments, the construct also comprises a sequence encoding a protease-cleavable linker. The fusion polypeptide encoded by the construct does not form part of a naturally occurring precursor polypeptide from which the polypeptide encoded by the transgene is released by proteolytic cleavage. In some embodiments, the transgene encodes a fusogenic polypeptide. The sequence encoding a protease-cleavable linker, if present, is positioned between the transgene and the sequence encoding a marker polypeptide.

The invention also provides a host cell comprising the nucleic acid construct of the preceding paragraph.

The invention also provides a kit for practicing the invention. The kit comprises the nucleic acid construct described above and one or more reagents for monitoring the release of the marker polypeptide.

The invention also provides a kit comprising a host cell transfected with the nucleic acid construct described above and one or more reagents for monitoring the release of the marker polypeptide.

These and other objects of the invention are provided by one or more of the embodiments described below.

One embodiment of the invention provides a nucleic acid construct for transfecting a cell with a transgene. The construct contains a sequence that encodes a marker polypeptide which serves as a detectable marker and a sequence that encodes a protease-cleavable linker peptide. When the transgene is expressed, the marker polypeptide and the linker are co-expressed in like amount. The linker is cleaved during normal post-translational processing by endogenous proteases within the cell to release a stoichiometric amount (i.e., a proportionate amount) of the marker polypeptide from the transgene product. The marker polypeptide is released from the cell where it is synthesized into extracellular fluid and is detectable in blood or other easily obtainable biological fluid samples and can be used to monitor the level and kinetics of expression of the transgene in the transfected cell or tissue. In a variation of this embodiment, the construct does not encode a protease-cleavable linker, but instead the marker polypeptide is regulated by a different promoter from that which regulates the transgene. In yet another variation of this embodiment, the construct does not encode a protease-cleavable linker, but instead the construct is transcribed to a polycistronic mRNA which comprises a ribosome entry site between the transgene and the sequence encoding the marker polypeptide.

Another embodiment of the invention provides a method for monitoring the expression of a transgene. The method employs the nucleic acid construct described in the preceding paragraph. A cell that has been transfected with this construct expresses the transgene as a fusion protein containing a marker polypeptide which is secreted from the cell and can be detected in blood or other easily obtainable-biological fluid samples. The marker polypeptide is non-immunogenic and non-functional. The marker polypeptide is released from the cell where it is made into the extracellular fluid. The marker peptide serves only as a marker whose level and kinetics of expression parallel those of the transgene product.

Still another embodiment of the invention provides another method for monitoring the expression of a transgene. A cell that has been transfected with the nucleic acid construct described above is introduced into a patient who has been transfected with the same transgene. In this embodiment, the bulk of the target cells are transfected with the transgene but not transfected with the marker polypeptide or linker of this invention; the cell which has been transfected with the construct of this invention, including the transgene, the marker polypeptide, and the linker, is used merely for expression monitoring of the transgene and is present only in sufficient amount to allow detection of the marker polypeptide. The marker polypeptide is released from the transfected cell into the extracellular fluid and serves as an indicator of transgene expression. In a variation of this embodiment, the cell is transfected with a construct that does not encode a protease-cleavable linker. Instead, the marker peptide is regulated by a different promoter from that which regulates the transgene. In another variation of this embodiment, the cell is transfected with a construct that is transcribed to a polycistronic mRNA which comprises an internal ribosome entry site between the transgene and the sequence encoding the marker peptide. Because of the position of the ribosome entry site, both the transgene product and the marker peptide are expressed separately without the need for protease cleavage.

Yet another embodiment of the invention provides a method of monitoring a therapeutic transgene. In this embodiment, the nucleic acid construct of this invention is used to transfect a cell as per either of the two previous embodiments. In this case, the transgene is a therapeutic gene which is introduced into the patient to remedy a functional deficiency, treat a pathological condition, or destroy certain cells of the patient by the activity of the transgene product. The marker polypeptide released from the transfected cell is detected and the information obtained is used to gage the progress of therapy with the transgene. In some versions of this embodiment, a transgene product which destroys cancer cells is monitored as a means of assessing the effectiveness of the therapy and deciding whether to repeat or adjust the therapy.

The invention thus provides the art with methods and materials for conveniently and effectively monitoring the level and kinetics of expression of transgenes in cells, tissues, animals or human patients without the need for disruptive and expensive sampling methods including surgery.

BRIEF DESCRIPTION OF THE DRAWINGS

FIG. 4 shows dose-response relationships for both cytopathic effects (per cent cell death, squares) and insulin C-peptide concentration in the culture medium (circles) as a function of the amount of DNA encoding measles H glycoprotein used for transfection. The DNA expression construct contained sequences encoding measles H glycoprotein, a furin-cleavable linker, and insulin C-peptide.

FIG. 5 presents the time course of C-peptide released into the medium of cultured TELCeB6 cells transfected with a construct which expresses C-peptide (CP1 GALV) and a construct which does not express C-peptide (Fus GALV).

Figure 6:
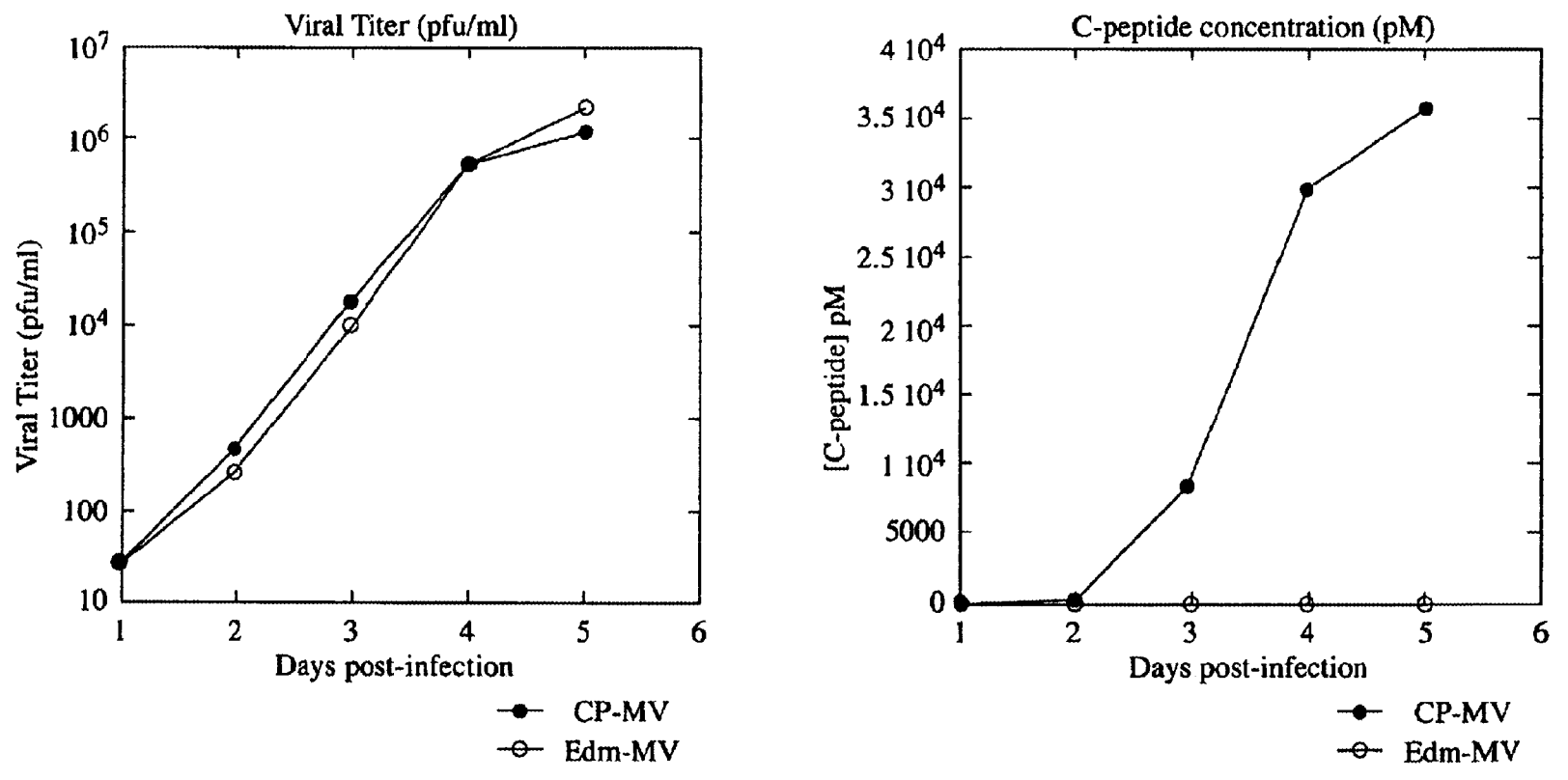

FIG. 6 shows the post-infection time course for both recombinant measles virus titer (left panel) and C-peptide concentration in the culture medium (right panel). Recombinant measles virions were generated using the chimeric H glycoprotein, and used to infect Vero cells at an MOI of 0.01.

FIG. 7 shows the effects of two cycles of concentration on the titer of the HIV-1 4070A transducing. Viral titer is increased 100-fold after concentration using the CaPO4 method.

DETAILED DESCRIPTION OF THE INVENTION

The inventors have developed a novel strategy for monitoring the expression of transgenes in vivo. An easily quantifiable marker polypeptide which preferably is non-immunogenic and biologically inactive is genetically fused to the N-terminus or the C-terminus of the product of the therapeutic transgene through a linker peptide that is cleavable by a cell-associated protease. Expression of the therapeutic transgene then results in the formation of a fusion protein carrying a protease-cleavable N or C-terminal peptide extension. The protease-cleavage signal is chosen such that at some point during the subsequent folding, assembly, and transport of the molecule within the cell, a cell-associated protease cleaves the peptide from the transgene product, and the peptide is released from the cell into the extracellular fluid. The term "cell-associated protease" includes any protease within the cell, such as a protease located in the cytoplasm or within or associated with an organelle. It also includes any protease associated with the cell, e.g., a protease located on the cell surface or in the extracellular space near the cell surface, such that the protease would cleave a peptide with the appropriate sequence near the cell surface. A constant relationship should exist between the level of expression of the therapeutic transgene and the amount of marker polypeptide released from the genetically modified cell.

A transgene is any nucleic acid sequence introduced into a cell which does not initially contain that sequence and which encodes a polypeptide of interest. Transgenes can be applied to remedy a disease condition in the process known as gene therapy. The term gene therapy can be applied to any therapeutic procedure in which genes or genetically modified cells are administered for therapeutic benefit. Any transgene can be used with the invention, although therapeutic transgenes are preferred. For some uses of the invention the transgene will be one which encodes a polypeptide that selectively kills a certain group of undesired cells such as cancer cells. For example, the transgene can encode a fusogenic polypeptide such as a viral fusion protein or an artificial polypeptide which causes the fusion of cells expressing the polypeptide, resulting in syncytium formation and cell death. The transgene can be introduced into a target cell or host cell by any mechanism of transfer known in the art, including any type of gene therapy, gene transfer, transfection, and the like.

Figure 1:
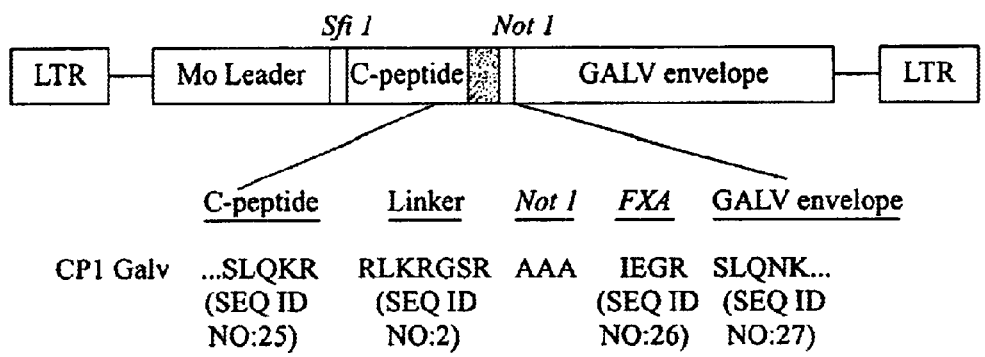
FIG. 1 displays an expression construct of insulin C-peptide linked to the N-terminus of gibbon ape leukemia virus (GALV) envelope protein via a furin cleavage linker (RLKRGSR; SEQ ID NO:2).

As used herein, the term "marker polypeptide" refers to a polypeptide that is used to monitor the expression of a transgene and is readily detectable in biological fluid samples. Preferably, the marker polypeptide is non-immunogenic, meaning that it is not likely to produce any significant immune response in the host organism undergoing gene therapy with the marker polypeptide. Not only might an immune response raised against the marker polypeptide be deleterious to the host organism, particularly if repeated bouts of gene therapy are required, but the production of antibodies reacting with the marker polypeptide would also accelerate the kinetics of removal of the marker polypeptide from the host and complicate its detection using immunological methods. The marker polypeptide is also preferably non-functional, which means that it lacks any significant known biological activity other than that required to serve its use as a marker (i.e., an activity that is detectable). Both the properties of non-immunogenicity and non-functionality are merely intended to improve the performance of the marker polypeptide by preventing undesirable side effects in the host organism. The requirements of non-immunogenicity and non-functionality are not intended to be absolute, and it is understood that a marker polypeptide of the invention may possess an insignificant remnant of biological activity or immunogenicity in the host organism and may possess significant immunogenicity or biological activity in an organism other than the host organism.

For some uses of the invention, the marker polypeptide is also preferably not part of a naturally occurring precursor polypeptide from which the transgene of interest is released by proteolytic cleavage. Instead, it is preferred that the marker polypeptide be selected either from a different naturally occurring polypeptide precursor or from a completely artificial sequence.

As used herein, the term "extracellular body fluid" encompasses any body fluid that is not the intracellular fluid, including but not limited to extracellular fluids such as blood, urine, interstitial fluid, cerebrospinal fluid lymph, etc.

For optimal monitoring of the expression of the transgene, expression of the marker polypeptide should be linked to the expression of the therapeutic transgene such that there is a fixed stoichiometric relationship between the expression of the two genes. In addition, the marker polypeptide should have the following properties: (1) It is preferably small (molecular weight below 10 kD) and soluble in biological fluids so as to allow rapid equilibration between the interstitial and intravascular fluid spaces. Larger marker polypeptides up to 100 kD can also be used, but allowance must be made for the kinetics of release of such larger peptides from the cell of origin and their transport into and removal from the biological fluid being tested. (2) There should be a convenient, sensitive, specific, and accurate assay available for detection of the peptide. (3) The biodistribution, metabolism and excretion of the peptide should be well characterized and its plasma half-life should be known. (4) The background level of expression of the marker polypeptide should be negligible in peripheral blood or other tested biological fluid. Alternatively, there should be a reliable method whereby the background levels of the marker polypeptide can be discounted in the interpretation of the assay.

This gene marking strategy is useful for monitoring the expression of a variety of both cell-associated and cytoplasmic transgene products. The use of a variety of different peptides is envisaged. Naturally occurring peptides with a very low background level of expression are ideally suited to this application since they are unlikely to be immunogenic. Biologically inactive peptide fragments derived from prohormone processing are particularly suited for use in the invention. For example, insulin is synthesized as a biologically inactive prohormone, proinsulin, which is cleaved to release insulin and biologically inactive C-peptide. Plasma levels of these products in humans are: proinsulin, 3–20 pmol/l; fasting insulin, 43–186 pmol/l; and C-peptide, 170–900 pmol/l. Endogenous insulin and C-peptide can be suppressed using somatostatin for improved background correction, and C-peptide peripheral kinetics have been extensively studied in both normal volunteers and diabetic patients. Patients with type I diabetes do not synthesize insulin and therefore have zero background levels of C-peptide (K. S. Polonsky et al., J. Clin. Invest. 77: 98–105 (1986)). An assay for quantifying C-peptide in human blood is described in P. C. Kao et al., Ann. Clin. Lab. Science 22: 307–316 (1992).

Other useful peptide fragments result from the processing of proopiomelanocortin, preproenkephalin, preprodynorphin, preprovasopressin, preprooxytocin, preprocorticotrophin releasing factor, preprogrowth hormnone releasing factor, preprosomato statin, preproglucagon, preprogastrin, preprocalcitonin, preproepidermal growth factor, preprobradykinin, preangiotensinogen, preprovasoactive intestinal peptide and other peptide hormone precursors (J. Douglass et al., Ann. Rev. Biochem. 53: 665–715 (1984); D. H. Lynch and S. H. Snyder, Ann. Rev. Biochem. 55: 773–799 (1986); J. C. Hutton, Diabetalogia 37 (suppl. 2): S48–S56 (1994)).

Another source of biologically inactive peptide fragments is those derived from proteolytic processing of zymogens to generate active enzymes such as proteases. For example, many pancreatic proenzymes release an activation peptide during their trypsin-induced activation (see e.g., K. Mithofer et al., Anal. Biochem. 230: 348–350 (1995), which describes an assay for trypsinogen activation peptide used to diagnose or monitor acute pancreatitis). Most such peptides are small (less than 1 kDa) and rapidly excreted in the urine. Small, rapidly excreted polypeptides are well suited for urine tests to monitor transgene expression and for quick, semi-quantitative testing of whether a transgene has been successfully delivered or is still operational. Other proenzymes, such as procarboxypeptidase B, have larger activation peptides of about 10 kD (K. K. Yamamoto et al., J. Biol. Chem. 267: 2575–2581 (1992)) and are therefore suitable as serum or urine markers. The activation peptide of procarboxypeptidase B has been applied as a marker for pancreatitis (S. Appelros et al., Gut 42: 97–102 (1998)). Similar assays exist for activation peptides derived from a wide range of enzymatic cascade reactions and are used for the analysis of blood coagulation (see e.g., H. Philippou, Brit. J. Haem. 90: 432–437 (1995)).

Another source of marker polypeptides for the invention is the fragments derived from proteolytic inactivation of hormones, proteases, and other biologically active molecules. Caution should be exercised that such peptides, if used in the invention, are non-immunogenic and non-functional as described above.

Marker polypeptides can also be derived from tumor antigens, which are polypeptides produced in excessive amounts of specific tumor subtypes. These polypeptides are currently used to monitor the response of a tumor to chemotherapy and to monitor patients for relapse. Convenient, sensitive assays have been developed for these antigens. Examples of tumor antigens include CA125 (ovarian cancer), alphafetoprotein (AFP, liver cancer), carcinoembroyonic antigen (CEA, colon cancer), intact monoclonal immunoglobulin or light chain fragments (myeloma), and beta subunit of human chorionic gonadotrophin (HCG, germ cell tumors).

Another source of marker polypeptides is the inactive variants of naturally occurring peptides. Assays exist which can detect inactive fragments or sequence variants of a wide range of biologically active molecules. For example, a fragment or sequence variant derived from the active portion of any polypeptide hormone can be used as a marker. These include gastrin, renin, prolactin, adrenocorticotrophic hormone, parathyroid hormone, parathyroid hormone related polypeptide, arginine vasopressin, beta endorphin, atrial naturetic factor, calcitonin, insulin, insulin-like growth factor, glucagon, osteocalcin, erythropoietin, thrombopoietin, human growth hormone, and others. Analogous hormones from other non-human species are also a source of peptide sequences which could be adopted or modified to serve as a marker polypeptide in the invention. Many of the commercially available assays for such hormones have the power to detect biologically inactive, truncated, or point-mutated variants of the natural polypeptide. For example, deletion of the first six N-terminal amino acids of parathyroid hormone (an 84 residue polypeptide whose normal blood level is 1.0–5.2 pmol/l) destroys biological activity, but the truncated molecule is still detectable using a standard immunoassay.

Unprocessible variants of naturally occurring precursor polypeptides can also serve as marker polypeptides. For example, proinsulin is processed to insulin and C-peptide by cellular proteases that cleave the junctions between the C-peptide and the A and B chains. Processing can be inhibited by mutation of these cleavage sites, such that the inactive, point-mutated proinsulin (normal level 3–20 pmol/l) will be released from the cell and detected in the blood. Similarly, variants of naturally occurring polypeptides with prolonged circulating half-lives can be used as marker polypeptides. Peptide elimination can be reduced by modifications that increase size or anionic charge (reduced glomerular filtration), by mutations in the recognition sites for inactivating proteases, and by mutations that lead to loss of receptor binding activity (reduced receptor-mediated clearance) (C. McMartin, Biochem. Soc. Trans. 17: 931–934 (1989)).

Fully synthetic or non-human peptides are also useful as marker polypeptides. Such peptides have been used to monitor protein expression and to track synthetic proteins during purification (e.g., FLAG tag, myc tag, strep tag). Similar peptides can be designed which lack immunogenicity in humans.

Central to the use of the invention is the creation and/or use of a nucleic acid construct comprising sequences encoding a transgene, a marker polypeptide, and optionally a protease-cleavable linker. The nucleic acid construct can be an expression vector, a plasmid that can be prepared and grown in bacteria, or an engineered virus capable of transfecting the host cell. The nucleic acid sequences of the construct can contain DNA, RNA, a synthetic nucleic acid, or any combination thereof, as known in the art. The nucleic acid construct can be packaged in any manner known in the art consistent with its delivery to the target cell. For example, the construct can be packaged into a liposome, a DNA- or retro-virus, or another structure. The sequences should be arranged so that the protease-cleavable linker peptide, if one is included, is situated between the transgene product and the marker polypeptide, resulting in the cleavage of the marker polypeptide from the transgene product by a selected protease, which can be a protease that is encountered in the host cell or organism during post-translational processing. One means of accomplishing this is to design the nucleic acid construct such that the sequences encoding both the marker polypeptide and the linker polypeptide are attached to either the 3' end or the 5' end of the transgene. The sequences encoding each of the three components may be interspersed with other sequences as needed. However, in order for the marker polypeptide to be cleaved from the transgene product during processing, it is necessary that the protease cleavable linker sequence be interposed between the transgene product and the marker polypeptide.

Preferably, the sequences encoding each of the three components (the transgene product, the linker, and the marker polypeptide) are all under control of a single promoter sequence, resulting in the expression of a fusion protein containing each of the three elements. This assures that the marker and the transgene product will be synthesized in stoichiometric proportion, which is preferred because it enhances the value of the marker as an indicator of the level of transgene expression. The chosen promoter can be one which regulates the expression of the transgene in a manner consistent with its use in the host organism, for example, in a manner consistent with the intended gene therapy. The expression of the marker polypeptide can be driven from a second promoter inserted:into the construct or it can be encoded on the same transcript as the transgene, but translated from an internal ribosome entry site. The use of two or more separate promoters is less likely to produce the desired stoichiometry of expression and more likely to complicate the relationship between release of the marker polypeptide and the expression of the transgene. However, the use of two promoters can, in some embodiments, obviate the need for including a protease-cleavable linker peptide. If the marker polypeptide is regulated by a separate promoter, it will be translated separately from the transgene product and released from the cell without requiring proteolysis. While the two promoters regulating the transgene and the marker polypeptide can be different, they can also be the same promoter, in which case the expression of both transgene and marker polypeptide are quite likely to be parallel, thereby increasing the effectiveness of the marker polypeptide for monitoring expression of the transgene.

Another alternative strategy to using a protease-cleavable linker is to include an internal ribosome entry site in the construct between the transgene or the coding sequence for the therapeutic polypeptide and the coding sequence for the marker polypeptide. Internal ribosomal entry sites (IRES, also called ribosomal landing pads) are sequences that enable a ribosome to attach to mRNA downstream from the 5' cap region and scan for a downstream AUG start codon, for example in polycistronic mRNA. *See generally*, Miles et al., U.S. Pat. No. 5,738,985 and N. Sonenberg and K. Meerovitch, Enzyme 44: 278–91 (1990). Addition of an IRES between the coding sequences for the transgene product and the marker peptide can enable the independent translation of either the transgene product or the marker peptide from a dicistronic or polycistronic transcript. IRES sequences can be obtained from a number of RNA viruses (e.g., picornaviruses, hepatitis A, B, and C viruses, and *influenza* viruses) and DNA viruses (e.g., adenovirus). IRES have also been reported in mRNAs from eukaryotic cells (Macejak and Sarnow, Nature 353: 90–94 (1991) and Jackson, Nature 353: 14015 (1991)). Viral IRES sequences are detailed in the following publications:
Coxsackievirus
   Jenkins, O., J. Gen. Virol. 68: 1835–1848 (1987)
   Iizuka, N. et al., Virology 156: 64–73 (1987)
   Hughes et al., J. Gen. Virol. 70: 2943–2952 (1989)
Hepatitis A Virus
   Cohen, J. I. et al., Proc. Natl. Acad. Sci. USA 84: 2497–2501 (1987)
   Paul et al., Virus Res. 8: 153–171 (1987)
Poliovirus
   Racaniello and Baltimore, Proc. Natl. Acad. Sci. USA 78: 4887–4891 (1981)
   Stanway, G. et al., Proc. Natl. Acad. Sci. USA 81: 1539–1543 (1984)
Rhinovirus
   Deuchler et al., Proc. Nati. Acad. Sci. USA 84: 2605–2609 (1984)
   Leckie, G., Ph.D. thesis, University of Reading, UK
   Skern, T. et al., Nucleic Acids Res. 13: 2111 (1985)
Bovine Enterovirus
   Earle et al., J. Gen. Virol. 69: 253–263 (1988)
Enterovirus Type 70
   Ryan, M. D. et al., J. Gen. Virol. 71: 2291–99 (1989)
Theiler's Murine Encephalomyelitis Virus
   Ohara et al., Virology 164: 245 (1988)
   Peaver et al., Virology 161: 1507(1988)
Encephalomyocarditis Virus
   Palmenberg et al., Nucl. Acids Res. 12, 2969–2985 (1984)
   Bae et al., Virology 170, 282–287 (1989)
Hepatitis C. Virus
   Inchauspe et al., Proc. Natl. Acad. Sci. USA 88: 10293 (1991)
   Okamoto et al., Virology 188: 331–341 (1992)
   Kato et al., Proc. Natl. Acad. Sci. USA 87: 9524–9528 (1990)
*Influenza* Virus
   Fiers, W. et al., Supramol. Struct. Cell Biochem. (Suppl 5), 357 (1981)

The sequence of the *influenza* 5'-UTR is AGCAAAAG-CAGGGUAGAUAAUCACUCACUGAGUGA-CAUCAAAAUC (SEQ ID NO: 1). The 12 nucleotides underlined form the IRES and are conserved in all *influenza* mRNAs.

The host cell chosen to receive the construct can be found in situ within a patient chosen to undergo gene therapy with the construct, or the host cell can be a cell isolated from the patient or from another source and transfection with the construct can take place in vitro using standard techniques (e.g., the addition of calcium phosphate solutions or lipids known to induce transfection). The construct itself or a cell transfected in vitro with the construct can be introduced into the patient by any suitable means known in the art, such as by injection, ingestion, or implantation.

Once the construct has been introduced into the patient, the release of the peptide marker can be monitored to determine whether and how much expression of the transgene is occurring. A sample of an appropriate biological fluid or secretion is obtained from the patient and the concentration of the marker polypeptide in the fluid or secretion is determined. Any biological fluid or secretion known to the art can be employed, e.g., blood, urine, saliva, cerebrospinal fluid, mucous, or feces, but the choice of sample is likely to be determined by the target location of the construct within the body and the expected route of release and excretion of the marker polypeptide. Samples of the biological fluid can be obtained at any desired time interval following administration of the nucleic acid construct in order to monitor the effectiveness of transfection, the regulation of transgene expression, or the progress of therapy.

The presence of the marker polypeptide in the biological fluid sample can be evaluated by any qualitative or quantitative method known in the art. Immunologic assays such as ELISA or radioimmunoassay are preferred because of their specificity, sensitivity, quantitative results, and suitability for automation. Such assays are readily available in most medical facilities for a number of possible marker polypeptides such as insulin C-peptide and beta-HCG. Chromatographic methods such as HPLC, optionally combined with mass spectrometry, can also be employed. Other analytic methods are possible, including the use of specific color reagents, thin layer chromatography, electrophoresis, spectroscopy, nuclear magnetic resonance, and the like. While it is generally preferred that the marker polypeptide itself be non-functional, i.e., that it not possess any significant biological activity which might interfere with the patient's physiology or therapy, it is conceivable that the marker polypeptide can possess an enzyme activity which can itself be quantified and used as a means of detecting the marker in a biological fluid sample.

If the marker polypeptide is a naturally occurring peptide, such as a cleavage fragment of a peptide hormone precursor, then a significant background level of the marker polypeptide would probably be encountered even in the absence of any expression of the fusion protein encoded by the nucleic acid construct. The background level can be determined in a patient prior to administration of the construct and simply subtracted from the value determined after transfection. The difference is referable to marker polypeptide released through expression of the transgene. A more complicated situation occurs if the marker polypeptide is naturally present in the patient and fluctuates with physiological or pathological circumstances. In that case, the background rhythm or cycle of the marker must be known with sufficient certainty to permit its estimation and subtraction from the values determined post transfection. Alternatively, it may be possible to apply a strategy to suppress the background level of the marker polypeptide or its fluctuations via the use of drugs, modification of the patient's diet, or other suitable measures.

Depending on the degree of accuracy required, the level of expression of the transgene product can either be inferred from the concentration of marker polypeptide determined in a biological fluid sample or can be determined more accurately by calibration. The level of expression of transgene product is expressed as the amount of such product, in moles or mg, synthesized by the cell, tissue, organ, or entire organism which was the target of the gene therapy per unit time. For example, the level of expression can be quantified as the number of nanomoles of transgene polypeptide-produced, per gram- of tissue-per hour. Calibration of the marker polypeptide can be accomplished by quantifying both the marker polypeptide and the transgene product itself (e.g., by extracting the tissue making the transgene product and measuring the product directly.using HPLC, ELISA, radioimmunoassay, Western blot, or other suitable method) over a sufficient time period to permit extrapolation or determination of the stoichiometry between measured marker polypeptide in a given biological fluid sample and actual tissue level of transgene product. Without calibration, a stoichiometry must be estimated or assumed in order to accurately determine expression of transgene product. Even if an assumed stoichiometry is not accurate, it should allow at least qualitative or semi-quantitative tracking of transgene expression.

The invention permits a great deal of flexibility and discretion in terms of the choice of the protease cleavable linker peptide. The protease specificity of the linker is determined by the amino acid sequence of the linker. Specific amino acid sequences can be selected in order to determine which protease will cleave the linker; this is an important indication of the location of cleavage within the cell or following secretion from the cell and can have a major effect on the release of the marker polypeptide and its transportation through the body of the patient. The furin cleavage signal is ideal for cell-associated transgenes that are transported to the cell surface through the Golgi compartment. Cell surface receptors, such as the LDL receptor used for the treatment of hypercholesterolemia or chimeric T cell receptors used for retargeting T cells can therefore be marked using furin-cleavable peptides. For cytoplasmic proteins, it is necessary to use cleavage signals that are recognized by cytoplasmic proteases and to use peptides with appropriate hydrophilic/ hydrophobic balance so that they can escape across the plasma membrane. For marker peptides that must escape the cell via diffusion across the cell membrane, small molecular size (e.g., $\leq 10$ kDa) will advantageously promote egress of the peptide to the interstitial space.

Some proteases useful according to the invention are discussed in the following references: V. Y. H. Hook, *Proteolytic and cellular mechanisms in prohormone and proprotein processing*, R G Landes Company, Austin, Tex., USA (1998); N. M. Hooper et al., Biochem. J. 321: 265–279 (1997); Z. Werb, Cell 91: 439–442 (1997); T. G. Wolfsberg et al., J. Cell Biol. 131: 275–278 (1995); K. Murakami and J. D. Etlinger, Biochem. Biophys. Res. Comm. 146: 1249–1259 (1987); T. Berg et al., Biochem. J. 307: 313–326 (1995); M. J. Smyth and J. A. Trapani, Immunology Today 16: 202–206 (1995); R. V. Talanian et al., J. Biol. Chem. 272: 9677–9682 (1997); and N. A. Thornberry et al., J. Biol. Chem. 272: 17907–17911 (1997). A variety of different intracellular proteases useful according to the invention and their recognition sequences are summarized in Table 1. While not intending to limit the scope of the invention, the following list describes several of the known proteases which might be targeted by the linker and their location in the cell.

Secretory Pathway (ER/Golgi/Secretory Granules)
  Signal peptidase
  Proprotein convertases of the subtilisin/kexin family (furin, PC1, PC2, PC4, PACE4, PC5, PC)
  Proprotein convertases cleaving at hydrophobic residues (e.g., Leu, Phe, Val, or Met)
  Proprotein convertases cleaving at small amino acid residues such as Ala or Thr
  Proopiomelanocortin converting enzyme (PCE)
  Chromaffin granule aspartic protease (CGAP)
  Prohormone thiol protease
  Carboxypeptidases (e.g., carboxypeptidase E/H, carboxypeptidase D and carboxypeptidase Z)
  Aminopeptidases (e.g., arginine aminopeptidase, lysine aminopeptidase, aminopeptidase B)
Cytoplasm
  Prolyl endopeptidase
  Aminopeptidase N
  Insulin degrading enzyme
  Calpain
  High molecular weight protease
  Caspases 1,2,3,4,5,6,7,8, and 9
    Cell Surface/pericellular Space
  Aminopeptidase N
  Puromycin sensitive aminopeptidase
  Angiotensin converting enzyme
  Pyroglutamyl peptidase II
  Dipeptidyl peptidase IV
  N-arginine dibasic convertase
  Endopeptidase 24.15
  Endopeptidase 24.16
  Amyloid precursor protein secretases alpha, beta and gamma
  Angiotensin converting enzyme secretase
  TGF alpha secretase
  TNF alpha secretase
  FAS ligand secretase
  TNF receptor-I and -II secretases
  CD30 secretase
  KL 1 and KL2 secretases
  IL6 receptor secretase
  CD43, CD44 secretase
  CD16-I and CD 16-II secretases
  L-selectin secretase
  Folate receptor secretase
  MMP 1, 2, 3, 7, 8, 9, 10, 11, 12, 13, 14, and 15
  Urokinase plasminogen activator
  Tissue plasminogen activator
  Plasmin
  Thrombin
  BMP-1 (procollagen C-peptidase)
  ADAM 1,2,3,4,5,6,7,8,9, 10, and 11
  Granzymes A, B, C, D, E, F, G, and H An alternative to relying on cell-associated proteases is to use a sequence encoding a self-cleaving linker. An example of such a sequence is that of the foot and mouth disease virus (FMDV) 2A protease. This is a short polypeptide of 17 amino acids that cleaves the polyprotein of FMDV at the 2A/2B junction. The sequence of the FMDV 2A propeptide is NFDLLKLAGDVESNPGP. The cleavage occurs at the C-terminus of the peptide at the final glycine-proline amino acid pair. Cleavage of FMDV 2A propeptide is independent of the presence of other FMDV sequences and can generate cleavage in the presence of heterologous sequences. Insertion of this sequence between two protein coding regions results in the formation of a self-cleaving chimera which cleaves itself into a C-terminal fragment which carries the C-terminal proline of the 2A protease on its N-terminal end, and an N-terminal fragment that carries the rest of the 2A protease peptide on its C-terminus (P. deFelipe et al., Gene Therapy 6: 198–208 (1999)). Thus, instead of using a cleavage signal recognizable by a cell-associated protease, the self-cleaving FMDV 2A protease sequence can be employed to link the marker polypeptide to the therapeutic polypeptide, resulting in spontaneous release of the marker polypeptide from the therapeutic protein.

An alternative to relying on cell-associated proteases is to use a sequence encoding a self-cleaving linker. An example of such a sequence is that of the foot and mouth disease virus (FMDV) 2A protease. This is a short polypeptide of 17 amino acids that cleaves the polyprotein of FMDV at the 2A/2B junction. The sequence of the FMDV 2A propeptide is NFDLLKLAGDVESNPGP (SEQ ID NO:4). The cleavage occurs at the C-terminus of the peptide at the final glycine-proline amino acid pair. Cleavage of FMDV 2A propeptide is independent of the presence of other FMDV sequences and can generate cleavage in the presence of heterologous sequences. Insertion of this sequence between two protein coding regions results in the formation of self-cleaving chimera which cleaves itself into a C-terminal fragment which carries the C-terminal proline of the 2A protease on its N-terminal end, and an N-terminal fragment that carries the rest of the 2A protease peptide on its C-terminus (P. deFelipe et al., Gene Therapy 6: 198–208 (1999)). Thus, instead of using a cleavage signal recognizable by a cell-associated protease, the self-cleaving FMDV 2A protease sequence can be employed to link the marker polypeptide to the therapeutic polypeptide, resulting in spontaneous release of the marker polypeptide from the therapeutic protein.

The above disclosure describes a method of monitoring transgene expression whereby the transgene is expressed as a fusion protein comprising the transgene product together with a marker polypeptide and a protease-cleavable linker peptide. With that method, it is anticipated that the construct encoding the fusion protein is used to transfect the cell, tissue, organ, or organism that is the target of gene therapy. The same nucleic acid construct can also be utilized in another fashion, whereby cells previously transfected with the construct (marker cells) are transferred to a patient to monitor transgene expression. In this embodiment, the actual transgenic therapy may or may not be accomplished using a separate vector that encodes only the transgene product and not the marker polypeptide or protease-cleavable linker fusion protein of the present invention. In this way, it is unnecessary to burden the bulk of the target cells with the additional genetic material, the synthesis of the marker and linker peptides, and the possible undesired side effects of the marker. Where the host cells for monitoring transgene expression are solely for monitoring purposes and not for treatment purposes, a cell of the patient or from another source is transfected in vitro using the construct of this invention. The transfected cell is introduced into the patient either concurrently with the introduction of a gene therapy vector, or shortly before or after the introduction of a gene therapy vector. Preferably, the cell carrying the construct of this invention is targeted to the same tissue or organ as-the therapeutic vector for optimal monitoring of the therapeutic transgene. Release of the marker polypeptide from the marker cells is used to monitor the expression level of the transgene as described above. The cell can alternatively be transfected with a construct that does not encode a protease-cleavable linker, but instead includes a second promoter which regulates the expression of the marker peptide. Another alternative is to transfect the cell with a construct that is transcribed to a polycistronic mRNA which comprises an internal ribosome entry site between the transgene and the sequence encoding the marker peptide. Because of the position of the ribosome entry site, both the transgene product and the marker peptide are expressed separately without the need for protease cleavage.

A nucleic acid or a host cell containing the nucleic acid may be administered in a pharmaceutical formulation, which comprises the nucleic acid or host cell mixed in a physiologically acceptable diluent such as water, phosphate buffered saline, or saline, and will exclude cell culture medium, particularly culture serum such as bovine serum or fetal calf serum, <0.5%. Administration may be intravenous, intraperitoneally, nasally, etc.

The dosage of nucleic acid or cells containing the nucleic acid will depend upon the disease indication and the route of administration but should be between 1–1000 µg of DNA/kg of body weight/day or 10,000–100,000,000,000 transfected cells/day. The duration of treatment will extend through the course of the disease symptoms and signs (clinical features), possibly continuously. The number of doses will depend upon disease delivery vehicle and efficacy data from clinical trials. Symptoms for a given disease are indicated by the conventional clinical description of the disease, and will be selected for monitoring by the physician treating the disease. For example, the symptoms of cancer are well-known for each type of cancer. One clinical sign for cancer assessment, for example, is tumor size, which can be measured as an indicator of disease response to treatment. When clinical symptoms are assessed, the physician monitors the symptoms and evaluates whether the symptoms are getting worse or better as the disease progresses or recedes, respectively. One such example is monitoring the destruction of certain cell types that are malignant as an indicator of the success of treatment.

Another embodiment of the present invention is a kit containing a nucleic acid construct according to the invention and one or more reagents for the detection of the marker polypeptide. Reagents for detecting the marker peptide can include, for example, a monoclonal antibody which binds the marker peptide and radiolabelled marker peptide suitable for radioimmunoassay, or a set of chemicals and appropriate antibodies to perform ELISA. An alternative kit would contain a marker cell that has previously been transfected with the construct together with one or more reagents for detection of the marker polypeptide. Either kit can include a set of instructions for using the construct or cell and for quantifying the marker polypeptide in a biological fluid sample.

EXAMPLE 1

Figure 2:
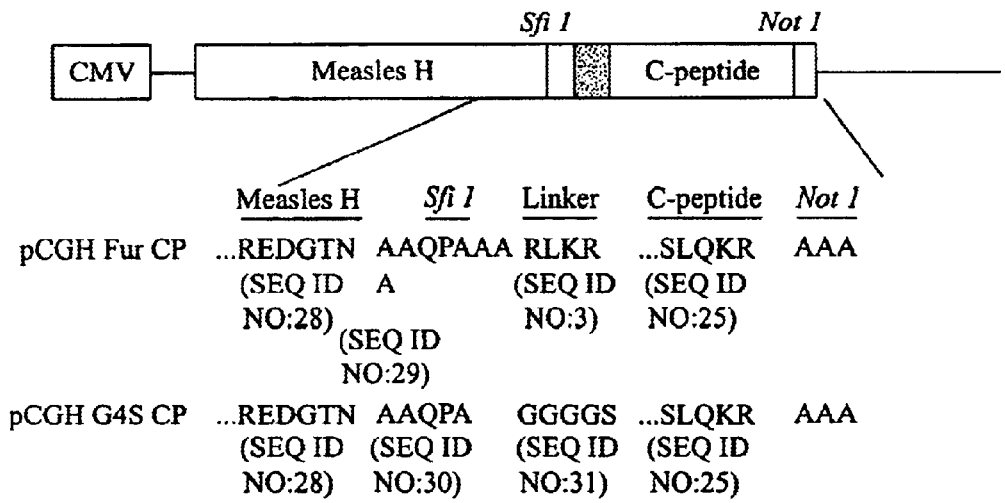
FIG. 2 displays an expression construct of insulin C-peptide linked to the C-terminus of measles virus H glycoprotein via a furin cleavable linker (RLKR; SEQ IN NO:3).

Construction of Fusogenic Membrane Glycoproteins (FMG) Linked to C-peptide Expression Plasmids Expression plasmids were prepared with insulin C-peptide linked to two different FMGs: gibbon ape leukemia virus (GALV) hyperfusogenic envelope lacking the cytoplasmic R-peptide and measles virus H glycoprotein. Expression constructs were made using furin-cleavable or non-cleavable linkers to connect the 33 amino acid C-peptide to either the N-terminus of GALV (FIG. 1) or the C-terminus of Measles H glycoprotein (FIG. 2).

EXAMPLE 2

Dose-response Study of the Expression of FMGs and C-peptide in Transfected Cell Lines The plasmid DNA of the various expression constructs were generated using a Qiagen Endofree Maxiprep Kit and the DNA was resuspended to a concentration of 1 µg/µl DNA in endotoxin-free Tris-EDTA buffer. The cell lines used in the transfection assays were TELCeB6 (for transfection with GALV constructs) or HT1080 cells (for transfection with measles H glycoprotein constructs).

The cells were plated at a density of $5 \times 10^5$ cells/well in a six-well plate and grown overnight. The next day, the cells were washed once in PBS and then transfected with different amounts of plasmid DNA using Superfect transfection agent (Qiagen). After 2 h at 37° C., the transfection media was removed, the cells were washed once in PBS and then incubated overnight in 1 ml/well of 6% FCS-DMEM.

The supernatants were harvested the next day from the respective wells, centrifuged briefly to remove cell debris, and frozen at −20° C. The samples were analyzed using ELISA by Mayo Medical Laboratories. The limit of detection of C-peptide in the assay was 33 pM.

After overnight incubation, syncytia were observed amongst the monolayer of transfected cells due to the expression of FMGs which cause cell-cell fusion. The cells were removed from the plates using trypsin and washed once in PBS. The number of viable cells were counted using trypan blue exclusion.

Figure 3:
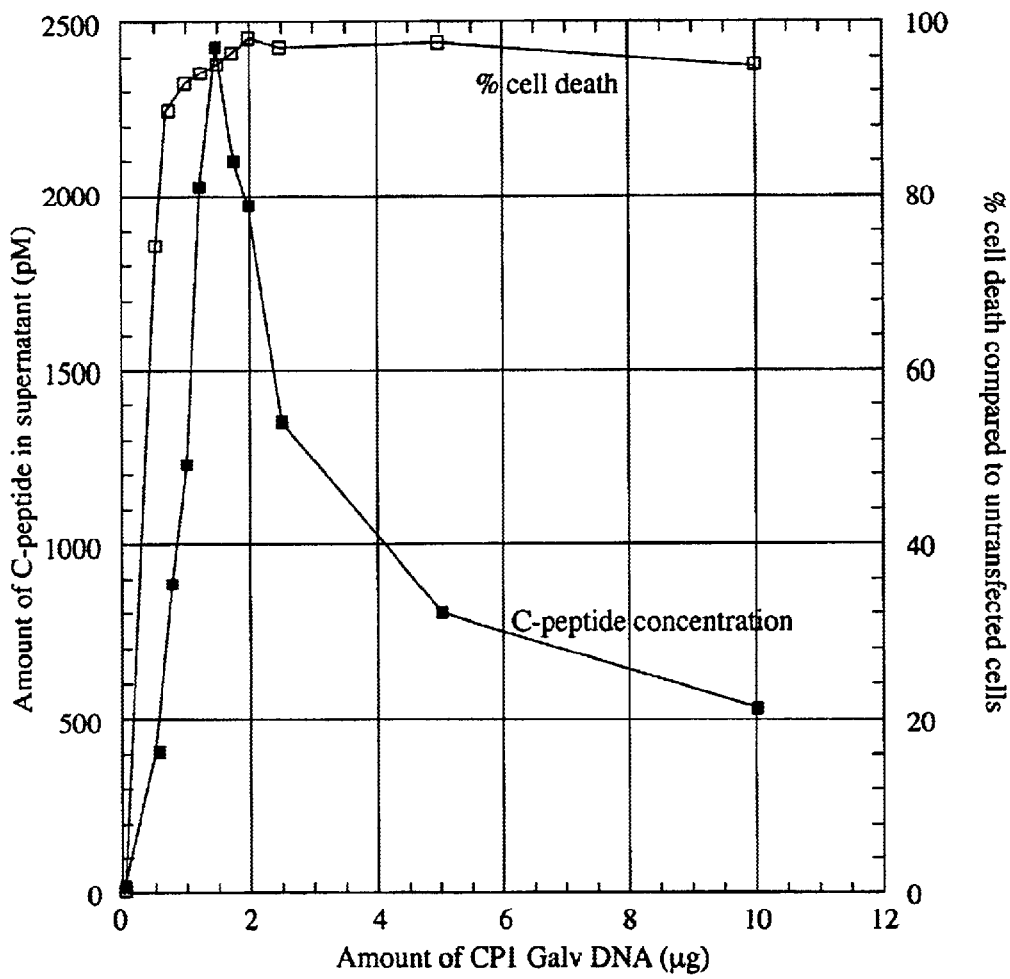
FIG. 3 shows dose-response relationships for both cytopathic effects (per cent cell death, squares) and insulin C-peptide concentration in the culture medium (circles) as a function of the amount of DNA encoding GALV envelope protein used for transfection. The DNA expression construct contained sequences encoding GALV envelope protein, a furin-cleavable linker, and insulin C-peptide.
Figure 4:
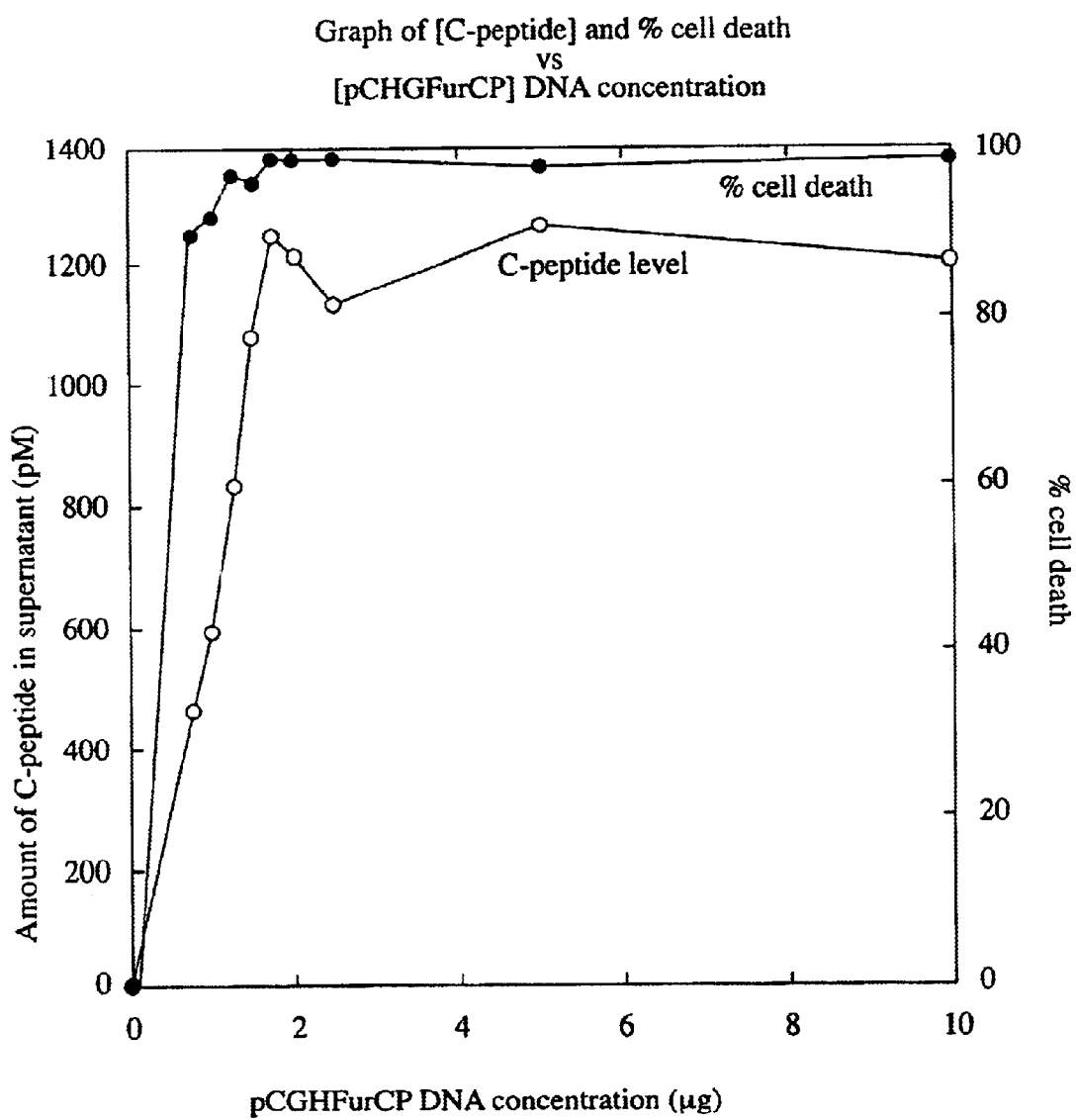

The results of the experiments are presented in FIGS. 3 and 4. Transfection with GALV or Measles H glycoprotein as the transgene resulted in massive syncytia formation in the monolayer of transfected cells, and only a very small percentage of the cells remained on the tissue culture well at the end of the overnight incubation. Most of the cells formed syncytia which floated off from the plates and were found in the supernatant. The cells left on the plates were trypsinized, and the number of viable cells was counted using trypan blue exclusion with a hemacytometer. Cell death is expressed as a percentage of the untransfected control (expressed as 100% viable). Together, these data demonstrate that there is a correlation between the quantity of plasmid used for cell transfection, the concentration of C-peptide in the culture supernatant and the magnitude of the cytotoxic effedt of the expressed membrane glycopeoteins.

EXAMPLE 3

Time Course of the Expression of FMGs and C-peptide in Transfected Cell Lines

Figure 5:
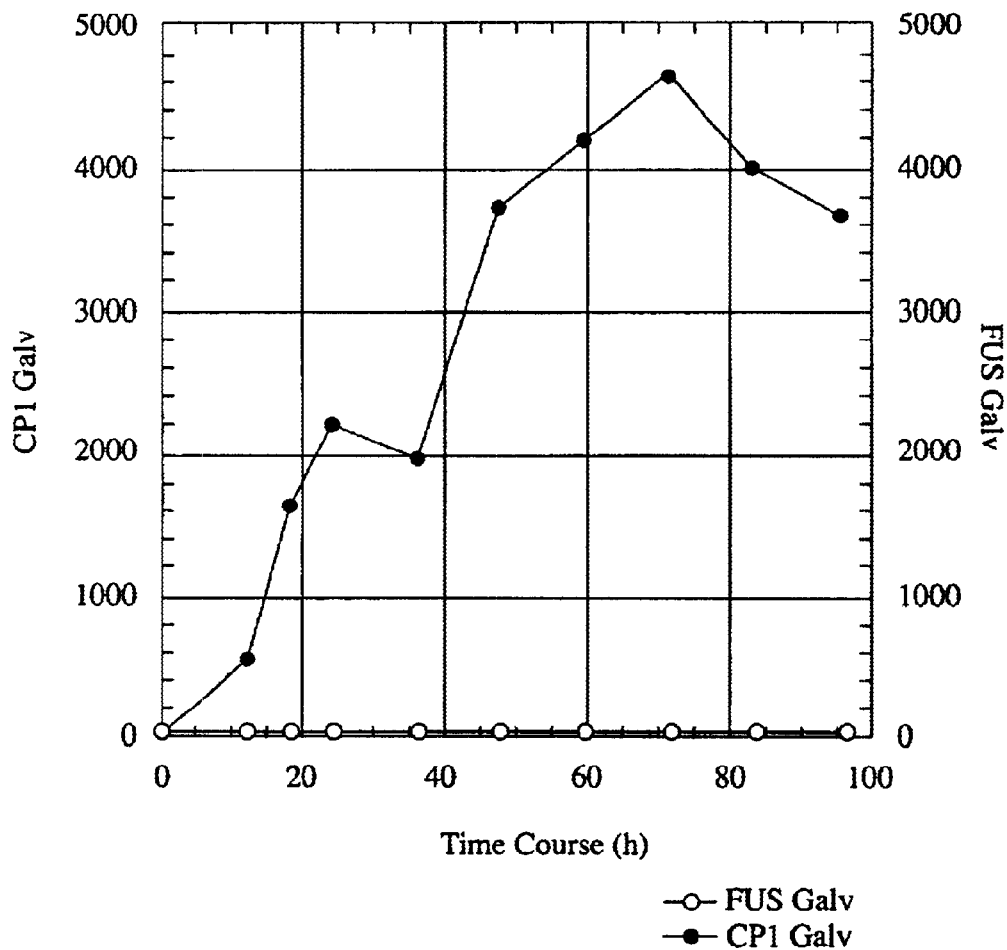

The target cells were plated at a density of $5\times10^5$ cells/well in a six-well plate as described above. The next day, the cells were transfected with 2.5 µg of plasmid DNA (Superfect, Qiagen) for 2 h at 37° C. The cells were washed once in PBS and incubated in 1 ml of 6% FCS-DMEM. At the respective time points, the supernatant was harvested from the respective wells, centrifuged briefly to remove cell debris, and the amount of C-peptide in the supernatant was analyzed. As shown in FIG. 5, the amount of C-peptide released into the supernatant increased with time.

EXAMPLE 4

Intratumoral Expression of GALV Linked to C-peptide

Nude mice are challenged with $5\times10^6$ A431 cells or HT1080 cells in 100 µl PBS administered subcutaneously into each flank. A431 is a human epithelial carcinoma cell line and HT1080 is a human fibrosarcoma cell line. Both form xenografts in nude mice. Tumor diameters are monitored daily after cell implantation, and when tumor diameter reaches 0.5 cm×0.5cm the tumors are injected with 50 µg of plasmid (CP1GALV or pHR'CMVLacZ or PBS as a control) complexed with 10 µg DMRIE:DOPE in a final volume of 80 µl PBS. Tumors are measured daily using calipers, and blood is drawn for C-peptide level determination at various intervals. Animals are monitored daily for signs of distress and are euthanized before tumor diameter reaches 2 cm or if they show signs of distress. At the time of euthanasia, tumors are excised for histological analysis. The concentration of C-peptide in the blood (a measure of the expression of GALV) is correlated with the size and histology of the tumors.

EXAMPLE 5

Intratumoral Expression of Measles F and Measles H Glycoproteins Linked to C-peptide Nude mice are challenged with $5\times10^6$ HT1080 cells in 100 µl PBS administered subcutaneously into each flank. Tumor diameters are monitored daily after cell implantation, and when tumor diameter reaches 0.5 cm×0.5 cm the tumors are injected with 50 µl of $1\times10^6$ HT1080 cells that were previously transfected with plasmids expressing measles F (pFQI) and measles H protein (pCGH Fur CP). F-expressing HT1080 cells transfected with pHR'CMVLac Z are used as controls. Tumors are measured daily using calipers and blood is drawn for C-peptide level determination at various intervals. Animals are monitored daily for signs of distress and are euthanized before tumor diameter reaches 2 cm or if they show signs of distress. At the time of euthanasia, tumors are excised for histological analysis. The concentration of C-peptide in the blood (a measure of the expression of measles F or measles H) is correlated with the size and histology of the tumors.

EXAMPLE 6

Intratumoral Expression of GALV Envelope Linked to C-peptide

In order to establish the relationship between the marker polypeptide level and the number of genetically modified cells, the intratumoral expression of GALV envelop linked to C-peptide is performed. CMT93 murine colorectal carcinoma cells are transfected with CP1GALV plasmid and selected in 50 µg per ml phleomycin. Stable transfectants are pooled and tested for release of C-peptide in the tissue culture medium. C-peptide accumulates rapidly. $2\times10^6$ of the transfected CMT93 (washed×3 in PBS and resuspended in 100 µl saline) are injected subcutaneously into each flank of 6 nude mice. C-peptide secreting CMT93 tumors grow at the sites of challenge. Tumor diameters are monitored daily and blood is sampled at regular intervals by tail vein bleeds for C-peptide level determination. C-peptide levels are plotted against tumor size/tumor cell number.

EXAMPLE 7

C-peptide Expression as a C-terminal Fusion to the H Glycoprotein of a Replicating Measles Virus The chimeric H glycoprotein was introduced into a full-length measles virus genome and the recombinant measles virus was rescued (Radecke et al., EMBO Journal 14: 5733–5784 (1995)). C-peptide was detectable in the supernatant of cultures infected with this recombinant measles virus, and by monitoring the concentration of C-peptide in culture supernatant, it was possible to follow the propagation of this virus in measles virus-infected cultures. Vero cell monolayers were infected at low (0.01) multiplicity of infection, and supernatant was harvested at varying time points thereafter for determination of C-peptide concentration and measles virus titer (FIG. 6).

EXAMPLE 8

Appearance of C-peptide in Urine as an Indirect Measure of In Vivo Viral Gene Expression The control and recombinant measles viruses were injected into human tumor xenografts grown in SCID) mice, and both urine and serum were collected for determination of human C-peptide levels. C-peptide-was not detectable in serum or urine-of control-animals, but was readily detected (43 pM–454 pM) in the urine of mice that had received intratumoral injections of the C-peptide expressing measles virus. These data establish the principle that C-peptide can be used as a marker of the presence and expression of a cell-associated transgene in vivo.

EXAMPLE 9

Lentiviral Vectors

The present invention provides a nucleic acid construct comprising sequences encoding a transgene, a marker polypeptide, and optionally a proteast cleavable linker, which, in one embodiment, can be contained within an engineered viral vector, such as lentiviral vectors. Strategies for manipulating the host/range properties of lentiviral vectors have been developed and tested in ex vivo tissue culture systems. VSVG pseudotyped lentiviral vector particles that were concentrated by ultracentrifugation were considered unsuitable for studies of systemic gene delivery because the clumping of pelleted viruses can significantly impact their biodistribution. Also, high-speed centrifugation destroys the integrity of lentiviral vectors pseudotyped with MLV envelopes. Accordingly, lentiviral vectors are produced without high-speed centrifugation, by a three plasmid co-transfection of 293 T cells and the vectors are harvested into serum-free DMEM, which is subsequently adjusted to pH7.7 by the addition of sodium hydroxide. Calcium chloride is then added to the vector containing supernatant (60 $\mu$M final concentration) and the fine precipitate of

TABLE 1

Concentration of HIV-1 supernatants using the CaPO4-coprecipitation method

| Vector | Initial titer | Final titer | % recovery | Volume ratio (initial:final) |
|---|---|---|---|---|
| 4070A-Luc | $1.16 \times 10^7$ RLU/ml | $1.99 \times 10^8$ RLU/ml | 66 | 26 |
| 4070A-Luc | $4.45 \times 10^6$ RLU/ml | $8.11 \times 10^7$ RLU/ml | 70 | 26 |
| 4070A-LacZ | $4.49 \times 10^6$ cfu/ml | $1.23 \times 10^8$ cfu/ml | 57 | 48 |

TABLE 1-continued

Concentration of HIV-1 supernatants using the CaPO4-coprecipitation method

| Vector | Initial titer | Final titer | % recovery | Volume ratio (initial:final) |
|---|---|---|---|---|
| VSV.G-Luc | $1.53 \times 10^7$ RLU/ml | $9.06 \times 10^7$ RLU/ml | 24 | 25 |
| VSV.G-Luc | $9.54 \times 10^7$ RLU/ml | $1.01 \times 10^9$ RLU/ml | 35 | 30 |
| VSV.G-LacZ | $8.53 \times 10^6$ cfu/ml | $1.29 \times 10^8$ cfu/ml | 57 | 26 | calcium phosphate is allowed to form at 37° C. The precipitate is then pelleted by low-speed centrifugation and the pellet is re-dissolved in 0.1 molar EDTA and dialyzed against phosphate buffered saline. All steps of the procedure have been optimized (Peng et al., manuscript in preparation).

Figure 7:
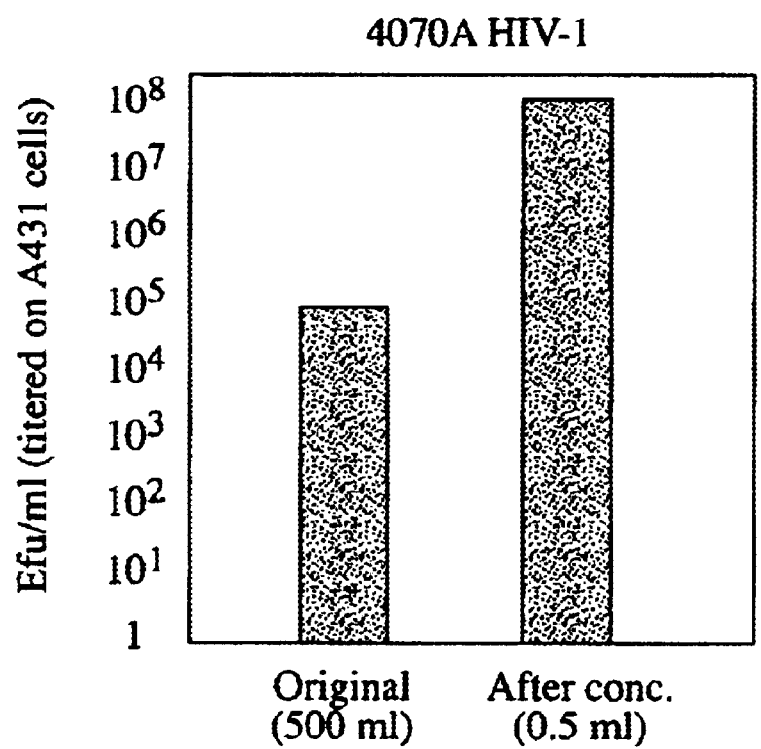

Using this approach, we are able to concentrate lentiviral vectors approximately 30-fold with each concentration cycle. Repeated concentration cycles are possible, and virus yields are typically of the order of 60–70 percent per concentration cycle. Table 1 shows that this procedure is applicable to VSVG pseudotyped lentiviral vector particles and to 4070A envelope pseudotyped vectors carrying either a β-galactosidase or luciferase marker gene. FIG. 7 shows that two cycles of concentration is sufficient to increase virus titer approximately 1,000-fold.

To determine whether luciferase is a suitable marker gene according to the present invention, concentrated stocks of luciferase lentiviral vectors were made, pseudotyped either with the VSVG envelope glycoprotein or with the 4070A MLV envelope glycoprotein. The concentrated vector was administered intravenously to nude mice at a dose of 500 $\mu$L of vector ($10^8$ RLU/ml) on three successive days. Mouse organs were harvested one week, two weeks and three weeks following vector administration, and luciferase activity in each of these organs was assayed using standard methods. The results of these experiments are shown in Table 2 and provide a clear demonstration that luciferase can be detected in the organs of these mice after systemic administration of concentrated lentiviral vectors.

TABLE 2

Luciferase activity (fg/20 $\mu$l) in livers of mice injected intravenously with 4070A-HIV-1 or VSVG-HIV-1

| | 4070A | | | | VSV.G | | |
|---|---|---|---|---|---|---|---|
| | 1st week | 2nd week | 3rd week | | 1st week | 2nd week | 3rd week |
| Liver | 148 | 213 | 149 | Liver | 24 | 461 | 164 |
| Spleen | 251 | 271 | 228 | Spleen | 98 | 596 | 296 |
| Heart | 149 | 138 | 161 | Heart | 0 | 365 | 13 |

TABLE 3

Properties of some proteases associated with post-translational processing.

| Protease | Subcellular Localization | Tissue Distribution | Cleavage Signal | Nucleotide Sequence |
|---|---|---|---|---|
| furin | Golgi | ubiquitous | RXKR (SEQ ID NO: 5) | tctnnnttttct (SEQ ID NO: 6) |
| MMP-2 | Golgi | tumor cells | PLGLWA (SEQ ID NO: 7) | cctaatcctaatacccgt (SEQ ID NO: 8) |

TABLE 3-continued

Properties of some proteases associated with post-translational processing.

| Protease | Subcellular Localization | Tissue Distribution | Cleavage Signal | Nucleotide Sequence |
|---|---|---|---|---|
| MT1-MMP | plasma membrane | tumor cells | PLGLWA (SEQ ID NO: 7) | cctaatcctaatacccgt (SEQ ID NO: 8) |
| caspase-1 | secretory pathway | ubiquitous | YEVDGW (SEQ ID NO: 9) | atccttcatctgcctacc (SEQ ID NO: 10) |
| caspase-2 | | | VDVADGW (SEQ ID NO: 11) | catctgcatcgtctgcctacc (SEQ ID NO: 12) |
| caspase-3 | | | VDQMDGW (SEQ ID NO: 13) | catctggtttacctgcctacc (SEQ ID NO: 14) |
| caspase-4 | | | LEVDGW (SEQ ID NO: 15) | aatcttcatctgcctacc (SEQ ID NO: 16) |
| caspase-6 | | | VQVDGW (SEQ ID NO: 17) | catgttcatctgcctacc (SEQ ID NO: 18) |
| caspase-7 | | | VDQVDGW (SEQ ID NO: 19) | catctggttcatctgcctacc (SEQ ID NO: 20) |
| alpha-secretase | secretory pathway | ubiquitous | amyloid precursor protein (APP) | amyloid precursor protein (APP) |
| proprotein convertase (subtilisin/kexin isozyme SKI-1) | endoplasmic reticulum | ubiquitous | brain neurotrophic growth factor precusor (RGLT) (SEQ ID NO: 21) | tctcctaattgt (SEQ ID NO: 22) |
| proprotein convertases (PC-2, PC-3, etc.) | secretory pathway | ubiquitous | | |
| tumor associated trypsin | | tumor cells | | |
| foot and mouth disease virus, protease 2A | | | NFDLLKLAGDVESNPGP (SEQ ID NO: 4) | ttgaagctgaataatttt aatcgtcctctgcatctt tcgttgggtcctggt (SEQ ID NO: 23) |

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A method of monitoring the production of a therapeutic polypeptide in a patient, said method comprising:
   (a) administering to said patient a nucleic acid construct encoding a therapeutic polypeptide and a marker polypeptide, wherein said marker polypeptide is releasable from a cell of said patient into an extracellular body fluid of said patient, wherein expression of said therapeutic polypeptide is regulated by a first promoter and expression of said marker polypeptide is regulated by a second promoter; and
   (b) detecting the presence or absence of said marker polypeptide above background in a sample of said extracellular body fluid, wherein the presence of said marker polypeptide above background in said sample is an indication that said therapeutic polypeptide is produced from said nucleic acid construct.

2. The method of claim 1, wherein said first and second promoters are identical.

3. The method of claim 1, wherein said therapeutic polypeptide is a fusogenic polypeptide.

4. The method of claim 1, wherein said marker polypeptide is a peptide fragment derived from a prohormone.

5. The method of claim 1, wherein said marker polypeptide is insulin C-peptide or beta-human chorionic gonadotrophin.

6. The method of claim 1, wherein said marker polypeptide is derived from a tumor antigen.

7. The method of claim 1, wherein said marker polypeptide is derived from carcinoembryonic antigen.

8. The method of claim 1, wherein said administering step comprises administering a virus containing said nucleic acid construct to said patient.

9. The method of claim 8, wherein said virus is a measles virus.

10. The method of claim 8, wherein said virus is a lentivirus.

11. The method of claim 1, wherein said background is zero.

12. The method of claim 1, wherein said sample is a urine sample.

13. The method of claim 1, wherein said sample is a blood sample.

14. A method of monitoring the expression of a transgene in a patient, said method comprising:
   (a) introducing a nucleic acid construct into a cell in said patient, wherein said nucleic acid construct comprises a transgene and a sequence encoding a marker polypeptide, wherein said marker polypeptide is releasable from cells of said patient into an extracellular body fluid of said patient, and wherein expression of said transgene is regulated by a first promoter and expression of said sequence encoding said marker polypeptide is regulated by a second promoter; and
   (b) detecting the presence or absence of said marker polypeptide above background in a biological sample of said patient, wherein the presence of said marker polypeptide above background in said biological sample is an indication that said transgene is expressed in said patient.

15. The method of claim 14, wherein said transgene encodes a fusogenic polypeptide.

16. The method of claim 14, wherein said marker polypeptide is a peptide fragment derived from a prohormone.

17. The method of claim 14, wherein said marker polypeptide is insulin C-peptide or beta-human chorionic gonadotrophin.

18. The method of claim 14, wherein said marker polypeptide is derived from a tumor antigen.

19. The method of claim 14, wherein said marker polypeptide is derived from carcinoembryonic antigen.

20. The method of claim 14, wherein said introducing step (a) comprises administering a virus containing said nucleic acid construct to said patient.

21. The method of claim 20, wherein said virus is a measles virus.

22. The method of claim 20, wherein said virus is a lentivirus.

23. The method of claim 14, wherein said background is zero.

24. The method of claim 14, wherein said biological sample is a urine sample.

25. The method of claim 14, wherein said biological sample is a blood sample.

26. A method of monitoring the expression of a transgene in a patient, said method comprising:
   (a) introducing a nucleic acid construct into a cell ex vivo, wherein said nucleic acid construct comprises a transgene and a sequence encoding a marker polypeptide, wherein expression of said transgene is regulated by a first promoter and expression of said sequence encoding said marker polypeptide is regulated by a second promoter;
   (b) introducing the cell of step (a) into said patient, wherein said marker polypeptide is releasable from cells of said patient into an extracellular body fluid of said patient; and (c) detecting the presence or absence of said marker polypeptide above background in a biological sample of said patient, wherein the presence of said marker polypeptide above background in said biological sample is an indication that said transgene is expressed in said patient.

27. The method of claim 26, wherein said transgene encodes a fusogenic polypeptide.

28. The method of claim 26, wherein said marker polypeptide is a peptide fragment derived from a prohormone.

29. The method of claim 26, wherein said marker polypeptide is insulin C-peptide or beta-human chorionic gonadotrophin.

30. The method of claim 26, wherein said marker polypeptide is derived from a tumor antigen.

31. The method of claim 26, wherein said marker polypeptide is derived from carcinoembryonic antigen.

32. The method of claim 26, wherein said introducing step (a) comprises infecting said cell of step (a) with a virus containing said nucleic acid construct.

33. The method of claim 32, wherein said virus is a measles virus.

34. The method of claim 32, wherein said virus is a lentivirus.

35. The method of claim 26, wherein said background is zero.

36. The method of claim 26, wherein said biological sample is a urine sample.

37. The method of claim 26, wherein said biological sample is a blood sample.

38. The method of claim 14 or 26, wherein said first and second promoters are identical.

39. The method of claim 14 or 26, wherein said transgene is therapeutic.

\* \* \* \* \*

UNITED STATES PATENT AND TRADEMARK OFFICE
CERTIFICATE OF CORRECTION

PATENT NO.      : 6,632,800 B1
DATED           : October 14, 2003
INVENTOR(S)     : Russell et al It is certified that error appears in the above-identified patent and that said Letters Patent is hereby corrected as shown below:

Title page,
Item [*] Notice, should read: -- Subject to any disclaimer, the term of this patent is extended or adjusted under 35 U.S.C. 154(b) by 0 days. --

Signed and Sealed this

Fifth Day of October, 2004

JON W. DUDAS
*Director of the United States Patent and Trademark Office*

SEQUENCE LISTING

<160> NUMBER OF SEQ ID NOS: 31

<210> SEQ ID NO 1
<211> LENGTH: 45
<212> TYPE: RNA
<213> ORGANISM: Influenza virus

<400> SEQUENCE: 1
agcaaaagca ggguagauaa ucacucacug agugacauca aaauc         45

<210> SEQ ID NO 2
<211> LENGTH: 7
<212> TYPE: PRT
<213> ORGANISM: Unknown
<220> FEATURE:
<223> OTHER INFORMATION: linker peptide

<400> SEQUENCE: 2

Arg Leu Lys Arg Gly Ser Arg
 1               5

<210> SEQ ID NO 3
<211> LENGTH: 4

```
<212> TYPE: PRT
<213> ORGANISM: Unknown
<220> FEATURE:
<223> OTHER INFORMATION: linker peptide

<400> SEQUENCE: 3

Arg Leu Lys Arg
 1

<210> SEQ ID NO 4
<211> LENGTH: 17
<212> TYPE: PRT
<213> ORGANISM: Foot-and-mouth disease virus

<400> SEQUENCE: 4

Asn Phe Asp Leu Leu Lys Leu Ala Gly Asp Val Glu Ser Asn Pro Gly
 1               5                  10                  15

Pro

<210> SEQ ID NO 5
<211> LENGTH: 4
<212> TYPE: PRT
<213> ORGANISM: Unknown
<220> FEATURE:
<223> OTHER INFORMATION: cleavage signal
<221> NAME/KEY: VARIANT
<222> LOCATION: (1)...(4)
<223> OTHER INFORMATION: Xaa = Any Amino Acid

<400> SEQUENCE: 5

Arg Xaa Lys Arg
 1

<210> SEQ ID NO 6
<211> LENGTH: 12
<212> TYPE: DNA
<213> ORGANISM: Unknown
<220> FEATURE:
<223> OTHER INFORMATION: cleavage signal
<221> NAME/KEY: misc_feature
<222> LOCATION: (1)...(12)
<223> OTHER INFORMATION: n = A,T,C or G

<400> SEQUENCE: 6
tctnnntttt ct                                                        12

<210> SEQ ID NO 7
<211> LENGTH: 6
<212> TYPE: PRT
<213> ORGANISM: Unknown
<220> FEATURE:
<223> OTHER INFORMATION: cleavage signal

<400> SEQUENCE: 7

Pro Leu Gly Leu Trp Ala
 1               5

<210> SEQ ID NO 8
<211> LENGTH: 18
<212> TYPE: DNA
<213> ORGANISM: Unknown
<220> FEATURE:
<223> OTHER INFORMATION: cleavage signal

<400> SEQUENCE: 8
cctaatccta atacccgt                                                  18
```

```
<210> SEQ ID NO 9
<211> LENGTH: 6
<212> TYPE: PRT
<213> ORGANISM: Unknown
<220> FEATURE:
<223> OTHER INFORMATION: cleavage signal

<400> SEQUENCE: 9

Tyr Glu Val Asp Gly Trp
 1               5

<210> SEQ ID NO 10
<211> LENGTH: 18
<212> TYPE: DNA
<213> ORGANISM: Unknown
<220> FEATURE:
<223> OTHER INFORMATION: cleavage signal

<400> SEQUENCE: 10
atccttcatc tgcctacc                                                   18

<210> SEQ ID NO 11
<211> LENGTH: 7
<212> TYPE: PRT
<213> ORGANISM: Unknown
<220> FEATURE:
<223> OTHER INFORMATION: cleavage signal

<400> SEQUENCE: 11

Val Asp Val Ala Asp Gly Trp
 1               5

<210> SEQ ID NO 12
<211> LENGTH: 21
<212> TYPE: DNA
<213> ORGANISM: Unknown
<220> FEATURE:
<223> OTHER INFORMATION: cleavage signal

<400> SEQUENCE: 12
catctgcatc gtctgcctac c                                               21

<210> SEQ ID NO 13
<211> LENGTH: 7
<212> TYPE: PRT
<213> ORGANISM: Unknown
<220> FEATURE:
<223> OTHER INFORMATION: cleavage signal

<400> SEQUENCE: 13

Val Asp Gln Met Asp Gly Trp
 1               5

<210> SEQ ID NO 14
<211> LENGTH: 21
<212> TYPE: DNA
<213> ORGANISM: Unknown
<220> FEATURE:
<223> OTHER INFORMATION: cleavage signal

<400> SEQUENCE: 14
catctggttt acctgcctac c                                               21

<210> SEQ ID NO 15
<211> LENGTH: 6
<212> TYPE: PRT
```

```
<213> ORGANISM: Unknown
<220> FEATURE:
<223> OTHER INFORMATION: cleavage signal

<400> SEQUENCE: 15

Leu Glu Val Asp Gly Trp
 1               5

<210> SEQ ID NO 16
<211> LENGTH: 18
<212> TYPE: DNA
<213> ORGANISM: Unknown
<220> FEATURE:
<223> OTHER INFORMATION: cleavage signal

<400> SEQUENCE: 16
aatcttcatc tgcctacc                                                 18

<210> SEQ ID NO 17
<211> LENGTH: 6
<212> TYPE: PRT
<213> ORGANISM: Unknown
<220> FEATURE:
<223> OTHER INFORMATION: cleavage signal

<400> SEQUENCE: 17

Val Gln Val Asp Gly Trp
 1               5

<210> SEQ ID NO 18
<211> LENGTH: 18
<212> TYPE: DNA
<213> ORGANISM: Unknown
<220> FEATURE:
<223> OTHER INFORMATION: cleavage signal

<400> SEQUENCE: 18
catgttcatc tgcctacc                                                 18

<210> SEQ ID NO 19
<211> LENGTH: 7
<212> TYPE: PRT
<213> ORGANISM: Unknown
<220> FEATURE:
<223> OTHER INFORMATION: cleavage signal

<400> SEQUENCE: 19

Val Asp Gln Val Asp Gly Trp
 1               5

<210> SEQ ID NO 20
<211> LENGTH: 21
<212> TYPE: DNA
<213> ORGANISM: Unknown
<220> FEATURE:
<223> OTHER INFORMATION: cleavage signal

<400> SEQUENCE: 20
catctggttc atctgcctac c                                             21

<210> SEQ ID NO 21
<211> LENGTH: 4
<212> TYPE: PRT
<213> ORGANISM: Unknown
<220> FEATURE:
<223> OTHER INFORMATION: cleavage signal
```

```
<400> SEQUENCE: 21

Arg Gly Leu Thr
 1

<210> SEQ ID NO 22
<211> LENGTH: 12
<212> TYPE: DNA
<213> ORGANISM: Unknown
<220> FEATURE:
<223> OTHER INFORMATION: cleavage signal

<400> SEQUENCE: 22
tctcctaatt gt                                                              12

<210> SEQ ID NO 23
<211> LENGTH: 51
<212> TYPE: DNA
<213> ORGANISM: Foot-and-mouth disease virus

<400> SEQUENCE: 23
ttgaagctga ataattttaa tcgtcctctg catctttcgt tgggtcctgg t                   51

<210> SEQ ID NO 24
<211> LENGTH: 33
<212> TYPE: PRT
<213> ORGANISM: Unknown
<220> FEATURE:
<223> OTHER INFORMATION: C-peptide sequence

<400> SEQUENCE: 24

Glu Ala Glu Asp Leu Gln Val Gly Gln Val Glu Leu Gly Gly Pro
 1               5                  10                  15

Gly Ala Gly Ser Leu Gln Pro Leu Ala Leu Glu Gly Ser Leu Gln Lys
            20                  25                  30
Arg

<210> SEQ ID NO 25
<211> LENGTH: 5
<212> TYPE: PRT
<213> ORGANISM: Unknown
<220> FEATURE:
<223> OTHER INFORMATION: C-peptide sequence

<400> SEQUENCE: 25

Ser Leu Gln Lys Arg
 1               5

<210> SEQ ID NO 26
<211> LENGTH: 4
<212> TYPE: PRT
<213> ORGANISM: Unknown
<220> FEATURE:
<223> OTHER INFORMATION: restriction site

<400> SEQUENCE: 26

Ile Glu Gly Arg
 1

<210> SEQ ID NO 27
<211> LENGTH: 5
<212> TYPE: PRT
<213> ORGANISM: Unknown
<220> FEATURE:
<223> OTHER INFORMATION: envelope peptide
```

```
<400> SEQUENCE: 27

Ser Leu Gln Asn Lys
1               5

<210> SEQ ID NO 28
<211> LENGTH: 6
<212> TYPE: PRT
<213> ORGANISM: Measles virus

<400> SEQUENCE: 28

Arg Glu Asp Gly Thr Asn
1               5

<210> SEQ ID NO 29
<211> LENGTH: 8
<212> TYPE: PRT
<213> ORGANISM: Unknown
<220> FEATURE:
<223> OTHER INFORMATION: restriction site

<400> SEQUENCE: 29

Ala Ala Gln Pro Ala Ala Ala Ala
1               5

<210> SEQ ID NO 30
<211> LENGTH: 5
<212> TYPE: PRT
<213> ORGANISM: Unknown
<220> FEATURE:
<223> OTHER INFORMATION: restriction site

<400> SEQUENCE: 30

Ala Ala Gln Pro Ala
1               5

<210> SEQ ID NO 31
<211> LENGTH: 5
<212> TYPE: PRT
<213> ORGANISM: Unknown
<220> FEATURE:
<223> OTHER INFORMATION: linker peptide

<400> SEQUENCE: 31

Gly Gly Gly Gly Ser
1               5
```